United States Patent [19]

Slaugh

[11] Patent Number: 4,891,446

[45] Date of Patent: Jan. 2, 1990

[54] PROCESS FOR PREPARING ALDEHYDES FROM ALCOHOLS

[75] Inventor: Lynn H. Slaugh, Cypress, Tex.

[73] Assignee: Shell Oil Company, Houston, Tex.

[21] Appl. No.: 252,284

[22] Filed: Sep. 30, 1988

[51] Int. Cl.$^4$ .............................................. C07C 45/00
[52] U.S. Cl. .................................................. 568/485
[58] Field of Search ........................ 568/485, 487, 488

[56] References Cited

U.S. PATENT DOCUMENTS

| | | | |
|---|---|---|---|
| 3,558,716 | 1/1971 | Engelhardt et al. | 568/485 |
| 4,383,124 | 5/1983 | Graaf et al. | 568/485 |

FOREIGN PATENT DOCUMENTS

| | | | |
|---|---|---|---|
| 1108200 | 10/1955 | Fed. Rep. of Germany | 568/485 |
| 19251 | 9/1970 | Japan | 568/487 |
| 130708 | 10/1975 | Japan. | |
| 287919 | 2/1971 | U.S.S.R. | 568/485 |
| 572450 | 12/1977 | U.S.S.R. | 568/485 |
| 173004 | 12/1921 | United Kingdom | 568/485 |
| 825602 | 12/1959 | United Kingdom | 568/487 |

*Primary Examiner*—Werren B. Lone

[57] ABSTRACT

This invention relates to a process for converting saturated aliphatic primary alcohols to aldehydes by passing said alcohols over a fixed bed of brass catalyst particles at a temperature ranging from about 375° to about 550° C. in the presence of hydrogen passing over the bed at a gaseous hourly space velocity of greater than about 250 hour$^{-1}$ and recovering the product aldehyde from an effluent passing out of the fixed bed.

11 Claims, No Drawings

PROCESS FOR PREPARING ALDEHYDES FROM ALCOHOLS

FIELD OF THE INVENTION

This invention relates to a process for converting saturated aliphatic primary alcohols to the corresponding aldehydes by contacting said aldehydes with a brass catalyst in the present of hydrogen.

BACKGROUND OF THE INVENTION

Copper/zinc catalysts, particularly brass spelter catalysts have long been used commercially for the dehydrogenation of isopropyl alcohol to acetone. U.S. Pat. No. 3,558,716, issued Jan. 26, 1971, discloses a process for producing beta-branched aldehydes by means of dimerization/dehydrogenation utilizing a catalyst that can contain copper and zinc. However, in this reference the copper and zinc are in the form of the oxides rather than in the form of a metallic alloy such as brass.

In Japanese Pat. application 50-130780, published Oct. 16, 1975, saturated aliphatic primary and secondary alcohols are converted to their corresponding aldehydes and ketones utilizing as a catalyst brass rings. In this reference long catalyst life is obtained by operating at reduced pressures i.e., less than atmospheric. Exemplary pressures are given as 30–60 millimeters of mercury. The exemplification in this reference teaches a preconditioning of the catalyst with water prior to the reaction followed by the reaction with the appropriate alcohol in the presence of air. This preconditioning and carrying out of the reaction in air would be expected to convert the catalyst at least in part to oxides.

Applicant has found that the dehydrogenation of an alcohol with a brass catalyst in the presence of additional hydrogen can provide an enhanced catalyst life. The resultant product aldehydes are important chemical intermediates that can be converted to specific ethoxalates, carboxylic acids, amines, etc. which find use, for example, in the detergents area and in the oil additives area.

SUMMARY OF THE INVENTION

Invention relates to a process for converting a saturated aliphatic primary alcohol to the corresponding aldehyde by passing said alcohol over a fixed bed of brass catalyst particles at a temperature ranging from about 375 to about 550° C., in the presence of hydrogen passing over the bed at a gaseous hourly space velocity of greater than 250 hour$^{-1}$ and recovering the product aldehyde from a effluent passing out of the bed.

Providing hydrogen in excess of that produced by the reaction results in enhanced catalyst life.

DESCRIPTION OF THE PREFERRED EMBODIMENTS

The catalyst utilized in the process of the instant invention is a brass catalyst. It comprises a metallic alloy of copper and zinc. Additional additives or impurities may be present in the copper-zinc alloy without detracting from the efficacy of the catalyst. For example, lead, bismuth, tin, antimony, cadmium, iron, cobalt, nickel, phosphorus, sulfur, selenium, tellurium, arsenic, silver, silicon, chromium, manganese and other components may be found in commercial alloys of copper and zinc but would not detract from the use of the copper-zinc alloy as a catalyt in the process of the instant invention. A particularly desirable catalyst is the so-called brass spelter catalyst which is utilized in the industry to dehydrogenate isopropyl alcohol to acetone. One source for the brass spelter catalyst is Belmont Smelting and Refining Company, Brooklyn, N.Y.

The catalyst that is utilized in the fixed bed is in the form of particles. These particles may be in numerous sizes and shapes such as for example nuggets, rods, spheres, rings, trilobedcylinders and the like. Size of the particles is not critical. However, the sizes are usually optimized to minimize pressure drop across the reactor. Typical suitable sizes range from an average particle diameter of about 1 millimeter to an average particle diameter of about 10 millimeters, although larger or smaller sizes are not precluded.

Typically the brass catalyst will comprise from about 30 to about 85% by weight of copper with the balance, i.e., 70 to about 15% being zinc. More preferably, the brass catalyst will comprise from about 40 to about 70% by weight of copper and from about 60 to about 30% by weight of zinc. In a more preferred embodiment, the brass catalyst will comprise about 45 to about 60% by weight of copper and from about 55 to about 40% by weight of zinc. In the preferred embodiment wherein the brass spelter catalyst is utilized, the catalyst comprises about 52% by weight of copper and about 48% by weight of zinc.

The reactor utilized in the process of the instant invention is typically one utilized in the industry for heterogeneously catalyzed reactions. It may be a vertical packed column or a horizontal packed tubular reactor. The reaction temperatures typically range from about 375 to about 550° C., preferably from about 420 to about 530° C. The reaction pressure is typically atmospheric or greater. Suitable pressure range from about 1 to about 100 atmospheres, more preferably from about 1 to about 10 atmospheres.

The alcohol feedstock is typically fed to the reactor at a liquid hourly space velocity ("LHSV") ranging from about 0.1 to about 20 hour$^{-1}$, more preferably from about 0.5 to about 10 hour$^{-1}$. The feedstock may be contained in a solvent that is inert to the reaction conditions. Suitable solvents are for example cyclic and acyclic alkanes.

The feed alcohols are saturated aliphatic primary alcohols having carbon number ranging from about 5 to about 20, more preferably from about 7 to about 18. These alcohols are frequently referred to in the industries as detergent range alcohols. They are frequently the product of a hydroformylation process.

In the dehydrogenation of the alcohols to the corresponding aldehydes, hydrogen is produced as a by-product. It has been found, however, that in order to obtain good catalyst life or stability additional hydrogen should be added to the reactor. Thus, a key aspect to the process of the instant invention is the addition of hydrogen gas to the reaction in order to enhance catalyst life. The hydrogen may be added to the feedstock of alcohol which is subsequently fed into the reactor, or more typically two separate streams comprising alcohol and hydrogen are fed into the fixed bed reactor. In order to enhance catalyst life it is necessary that hydrogen by fed to the reactor at a gaseous hourly space velocity ("GHSV") of greater than 250 hour$^{-1}$, preferably greater than 500 hour$^{-1}$.

The alcohol passes through the reactor and in doing so is converted over the brass catalyst to the aldehyde. The effluent passing out of the reactor comprises hydrogen, product aldehyde, unreacted alcohol, any inert solvents utilized, as well as small amounts of by-products such as low boiling point oligomers. The product aldehyde is recovered from the effluent by conventional means, such as flash or multistage distillation. Unreacted alcohol is suitably recycled to the reactor.

The ranges and limitations provided in the instant specification and claims are those which are believed to particularly point out and distinctly claim the instant invention. It is, however, understood that other ranges and limitations that perform substantially the same function in substantially the same manner to obtain the same or substantially the same result are intended to be within the scope of the instant invention as defined by the instant specification and claims.

The process of the instant invention will be illustrated by the following examples which are provided for illustration are not to be construed as limiting the invention.

EXAMPLE 1

Brass Spelter catalyst was tested under a variety of conditions for the dehydrogenation of 1-nonanol. As catalyst was utilized 1068 Special Holtite Brazing Metal obtained from Belmont Smelting and Refining Company, Brooklyn, N.Y. This catalyst contained 52 w % copper and 48 w % zinc. The brazing metal was broken up into chunks falling within the range of 10–20 mesh. Five cubic centimeters of this material were loading into a ⅜ inch inside diameter reactor. Several runs were made at the various time-temperature-flow conditions as shown in Table 1. A pressure of 45 psig and a LHSV of 3.6 for the feed alcohol was maintained during the reaction. After the end of the run time the product sample was analyzed by gas-liquid chromatography. Conversions and selectivities to the aldehyde are shown in Table 1. Some cracking of the alcohol/aldehyde to hydrocarbons occurred and some dimerization of the alcohol and/or aldehyde occurred to $C_{18}$ products gen is dropped to about 240 hour$^{-1}$, the selectivity to the aldehyde product falls off dramatically.

TABLE 2

| SAMPLE NO. | RUN TIME. HRS. | H$^2$ FLOW, GHSV | % WT C$_9$ ALDEHYDE IN THE PRODUCT[a] |
|---|---|---|---|
| 2-1 | 54 | 3000 | 47 |
| — | 54 | 1500 | H$_2$ Rate Decreased at 54 Hr Run Time |
| 2-2 | 56 | 1500 | 50 |
| 2-3 | 96 | 1500 | 47.5 |
| 2-4 | 98 | 720 | 45 |
| 2-5 | 102 | 720 | 44.5 |
| 2-6 | 147 | 720 | 45.6 |
| — | 147 | 240 | H$_2$ Rate Decreased at 147 Hr Run |
| 2-7 | 153 | 240 | 19.6 |
| 2-8 | 171 | 240 | 16.8 |
| — | 171 | 3000 | H$_2$ Rate Increased at 171 Hr Run |
| 2-9 | 175 | 3000 | 48.5 |
| — | 179 | 480 | H$_2$ Rate Decreased at 179 Hr Run |
| 2-10 | 195 | 480 | 44.3 |
| 2-11 | 268 | 480 | 43.2 |
| — | 268 | 3000 | H$_2$ Rate Increased at 268 Hr Run |
| 2-12 | 270 | 3000 | 46.5 |

[a]The product also contained < 1% wt hydrocarbons and 2–4% wt C$_{18}$ products. At the lower H$_2$ flow rates the products were amber colored.

EXAMPLE 3

A 700-hour life test was conducted (420–450° C. 50 PSIG, alcohol LHSV - 4.8, H$_2$ flow varied), during which, the brass spelter catalyst was deliberately abused to ascertain just how robust the system is for the conversion of higher alcohols to aldehydes. Three different feeds were used, namely C$_9$, C$_{13}$ and C$_{15}$ alcohols. The catalyst gradually increased in activity over the first 150 hours (55–60% conversion) and then remained constant. After about 530 hours, the hydrogen flow rate

TABLE 1

| SAMPLE NO. | RXN TIME. HRS | RXN TEMP., °C. | H$_2$ FLOW GHSV | ALCOHOL FLOW LHSV | CONV. W % | SELECTIVITY, W% | | |
|---|---|---|---|---|---|---|---|---|
| | | | | | | NONANAL | HYDROCARBONS | C$_{18}$ PRODUCTS |
| 1-1 | 96 | 470 | 2400 | 3.6 | 72.7 | 93.0 | 2.35 | 4.65 |
| 1-2 | 118 | 480 | 2400 | 3.5 | 76.4 | 94.8 | 2.07 | 3.28 |
| 1-3 | 124 | 500 | 2400 | 3.5 | 83.3 | 94.5 | 2.54 | 3.00 |
| 1-4 | 126 | 500 | 1200 | 3.5 | 82.7 | 91.7 | 3.50 | 4.78 |
| 1-5 | 142 | 500 | 2400 | 3.5 | 83.3 | 94.3 | 2.38 | 3.36 |
| 1-6 | 144 | 520 | 2400 | 3.5 | 88.6 | 94.6 | 3.71 | 2.80 |
| 1-7 | 146 | 520 | 2400 | 5.2 | 85.6 | 94.3 | 3.60 | 2.06 |
| 1-8 | 148 | 520 | 2400 | 6.8 | 83.5 | 93.6 | 3.35 | 3.01 |
| 1-9 | 151 | 480 | 2400 | 4.2 | 72.5 | 95.7 | 1.55 | 2.72 |
| 1-10 | 170 | 480 | 2400 | 5.4 | 68.2 | 95.9 | 1.33 | 2.83 |
| 1-11 | 197 | 500 | 3600 | 3.4 | 82.2 | 94.2 | 1.74 | 4.07 |
| 1-12 | 200 | 520 | 3600 | 5.5 | 86.0 | 94.0 | 2.74 | 3.29 |

EXAMPLE 2

Experiment 1 was repeated with changes in the flow rate of the hydrogen at various points in the run to determine the effect of hydrogen on the selectivity of the catalyst. During the 200-hour run, the hydrogen flow rate was varied to determine the minimum amount required for catalyst stability. It was found at least 50 run hours were required for the catalyt to come up to full activity. Conditions were chosen (400° C., LHSV 3.6) to obtain alcohol conversion levels of about 45%. Product samples were analyzed at various times by gas-liquid chromatography. The results are shown in Table 2. As can be seen from Table 2 (Sample 2-7) when the gaseous hourly space velocity of the hydroover the 5 cc of 10–20 mesh catalyst was decreased from 250 cc/min. to zero. The catalyst lost most of its activity over the next 50 hours. When the H$_2$ flow was reinstated, normal activity resumed after several hours. The introduction of water (2 ml/hr) along with the C$_9$ alcohol feed again caused the catalyst to lose most of its activity, even though extra hydrogen was added. Once exposure to water vapor was stopped, the catalyst quickly regained its activity. There was little, if any activity loss over the full 700-hour life test period.

I claim:

1. A process for converting saturated aliphatic primary alcohols having numbers ranging from about 5 to about 20 to the corresponding aldehydes which comprises passing said alcohols over a fixed bed of brass catalyst particles at a temperature ranging from about 375 to about 550° C. in the presence of hydrogen passing over the bed at a gaseous hourly space velocity of greater than about 250 hour$^{-1}$ and recovering the product aldehydes from an effluent passing out of the fixed bed.

2. The process of claim wherein the brass catalyst particles comprise from about 30 to about 85 percent by weight of copper and from about 70 to about 15 percent by weight of zinc.

3. The process of claim 2 wherein the brass catalyst particles comprise from about 40 to about 70 percent by weight of copper and from about 60 to about 30 percent by weight of zinc.

4. The process of claim 3 wherein the brass catalyst particles comprise from about 45 to about 60 percent by weight of copper and from about 55 to about 40 percent by weight of zinc.

5. The process of claim 4 wherein the brass catalyst particles comprise about 52 percent by weight of copper and about 48 percent by weight of zinc.

6. The process of any one of claims 1-5 wherein the temperature ranges from about 420 to about 530° C.

7. The process of any one of claims 1-5 wherein the pressure ranges from about 1 to about 100 atmospheres.

8. The process of claim 7 wherein the pressure ranges from about 1 to about 10 atmospheres.

9. The process of any one of claims 1-5 wherein the alcohol is passed over the catalyst at a liquid hourly space velocity ranging from about 0.1 to about 20 hour$^{-1}$.

10. The process of claim 9 wherein the alcohol is passed over the catalyst at a liquid hourly space velocity ranging from about 0.5 to about 10 hour$^{-1}$.

11. The process of any one of claims 1-5 wherein the gaseous hourly space velocity of the hydrogen is greater than about 500 hour$^{-1}$.

* * * * *